United States Patent [19]
McClure

[11] 3,934,978
[45] Jan. 27, 1976

[54] METHOD FOR ASSAY OF PROSTAGLANDINS
[75] Inventor: William O. McClure, So. Pasadena, Calif.
[73] Assignee: Nelson Research & Development Co., Irvine, Calif.
[22] Filed: Oct. 7, 1974
[21] Appl. No.: 512,446

[52] U.S. Cl. .................................. 23/230 B; 424/7
[51] Int. Cl. ...................... G01n 21/00; G01n 31/08; G01n 33/16
[58] Field of Search ....................... 23/230 B; 424/7

[56] References Cited
OTHER PUBLICATIONS
N. Ambache et al., Brit. J. Pharmacol. 33, 162, (1968).
E. W. Horton, Physiological Review 49, 122, (1969).
N. H. Andersen, Chem. Abstr. 71, 27642p (1969).
E. Änggärd et al., J. Chromatogr. 48, 542, (1970).

Primary Examiner—Robert M. Reese
Attorney, Agent, or Firm—Martin A. Voet

[57] ABSTRACT

A method for assaying prostaglandins of the E and F series comprising the sequential steps of reducing the keto groups in a sample containing the prostaglandins to hydroxy groups, selectively oxidizing the prostaglandin 15-OH groups to keto groups, reducing the keto groups to hydroxy groups by means of a radioactive labeled chemical reducing agent, isolating radioactive labeled prostaglandins and measuring the amount of radioactivity of the isolated radioactive labeled prostaglandins.

10 Claims, No Drawings

METHOD FOR ASSAY OF PROSTAGLANDINS

BACKGROUND OF THE INVENTION

1. Field of the Invention

The present invention relates to a method of assay. More particularly, the present invention relates to a method of assay for prostaglandins of the E and F series.

2. Background of the Prior Art

Prostaglandins are a group of unsaturated hydroxy and hydroxy-keto long-chain carboxylic acids. These are widely distributed in human and animal tissues and possess a wide variety of pharmacological actions. It seems probable that prostaglandins have a biochemical role fundamental to many, perhaps all, animal cells. Many articles have been devoted to the prostaglandins especially the biochemical/pharmacological aspects. A recent review entitled, "Hypothesis on Physiological Roles of Prostaglandins" by E. W. Horton, Physiological Review, Volume 49, No. 1, January, 1969, reviews the present status of the knowledge on the functional significance of the prostaglandins.

Naturally occurring prostaglandins are 20-carbon fatty acids containing a cyclopentane ring. The parent saturated acid has been named prostanoic acid as drawn below:

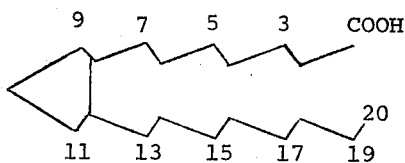

Two important series of natural prostaglandins are designated by the letters E and F corresponding to differences in the ring, as shown below:

All of the prostaglandins have a 15-hydroxyl substituent. The degree of unsaturation of the side chains is indicated by the subscript numeral after the letter: thus prostaglandin $E_1$ has a trans double bond in the 13 position, $E_2$ has, in addition, a cis double bond in the 5 position, $E_3$ has a third double bond in the 17 position, etc. The structural formulas of 14 naturally occurring prostaglandins are shown in FIG. 3 of the Horton reference, supra.

Prostaglandins have a wide variety of pharmacological actions, being active in such diverse areas as fertility, transport of sperm, menstruation, parturation, placental blood flow, gastric secretion, muscle contractility (including vascular smooth muscle, respiratory smooth muscle, gastrointestinal smooth muscle, uteral smooth muscle, and spleenic capsular smooth muscle), development of epidermal tissues and central nervous transmitters. Prostaglandins are also thought to affect permeability, e.g., the skin and the eye. Thus, it has been suggested that prostaglandins may act as mediators of various forms of inflammation. This role in inflammation is strongly supported by the involvement of prostaglandins in the inflammatory process in joints, skin, and eyes.

While assay methods are known for prostaglandins, they are generally difficult and/or inaccurate and/or inconvenient and time consuming. Furthermore, unknown compounds in variable biological samples, e.g. blood, urine, tissue, can make it difficult or impossible to obtain an accurate assay with methods known heretofore.

SUMMARY OF THE INVENTION

The prostaglandin assay method of the present invention overcomes the foregoing problems by providing a relatively rapid, accurate and convenient method for assay of prostaglandins which is independent of the biological sample which is assayed.

The method comprises the following sequential steps. Step (1) is chemically reducing the keto groups in a biological sample containing the prostaglandins to be assayed. The preferred method of reduction uses sodium borohydride ($NaBH_4$) as the reducing agent. In step (2), the 15-OH group of the prostaglandins is selectively oxidized. The preferred method is by reacting the sample with an enzyme, 15-hydroxy prostaglandin dehydrogenase (or $NAD^+$-hydroxy prostanoate oxidoreductase (E.C. 1.1.1.)). In step (3), the keto groups in the sample are reduced by a radioactive labeled reducing agent such as sodium borotritide ($NaB^3H_4$). This reduction step reduces the 15 keto groups on the prostaglandins (the only keto groups now remaining in the sample) to hydroxy groups which are $^3H$ labeled. In step (4), the radioactive labeled prostaglandins in the sample are separated from the sample, preferably by chromatography, and counted by conventional radiation counting techniques to determine the amount and concentration of prostaglandins of the E and F series in the sample.

If the sample contained no keto groups, it would not be necessary to utilize step 1. However, since it is generally not known whether a given biological sample contains any keto groups other than prostaglandin keto groups, the application of step 1 ensures that the only keto groups which can react in step 3 are prostaglandin 15-keto groups. If step 1 were not utilized, other radioactive labeled keto groups might inadvertently be counted as prostaglandins.

DETAILED DESCRIPTION OF THE REACTION

The step 1 reduction reaction utilizes a reducing agent such as sodium borohydride and takes place by reacting the biological sample in an excess of sodium borohydride in a suitable solvent, for example, alcohols, such as, for example, methanol, ethanol, propanol, isopropanol, etc. and water, at temperatures between about 0°–75°C and preferably about 20°–30°C for a period of time sufficient to complete the reaction. Reaction time generally varies from 0.1–10 hours and preferably 0.1–2 hours.

In selectively oxidizing the 15-OH group of the prostaglandins to form a 15-keto group (step 2), known procedures are used. The preferred procedure is selective oxidation of the 15-OH group on the prostaglandin by reacting the sample with 15-hydroxy prostaglandin dehydrogenase and $NAD^+$ to form the 15-keto prostaglandin + NADH. The appropriate enzyme can be obtained from various sources. The preferred source is swine lung. A partial purification of the enzyme can be obtained via conventional procedures such as differential centrifugation, ammonium sulfate precipitation and ion-exchange chromatography, although a crude supernatant fraction is sufficient for the reaction. For example, the reaction utilizes a sufficient quantity of enzyme (1–20 mg) in the presence of excess $NAD^+$ (1–50 mM) at a basic pH (8.0–9.0) in a solution of 50 mM Tris.HCl, 50 mM KCl, 10 mM $MgCl_2$ and 7 mM 2-mercaptoethanol. Reaction time varies from 0.1–10 hours and preferably 0.1 to 1 hour.

The reduction reaction of sodium borotritide and a biological sample containing prostaglandin (step 3) takes place by reacting an excess of sodium borotritide in a suitable solvent, for example, alcohols, such as, for example, methanol, ethanol, propanol, isopropanol, water, 2,2-dimethoxypropane, etc. at temperatures between about 0°–75°C and preferably about 20°–30°C for a period of time sufficient to complete the reaction. Reaction time generally varies from 0.1–10 hours and preferably 0.1–2 hours.

The tritiated prostaglandins are then isolated from the reaction mixture (step 4) by any suitable analytical method including thin layer chromatography (TLC), paper chromatography, column chromatography, etc. and preferably TLC. The isolated, tritiated prostaglandins are then evaluated for radioactivity by conventional radiation counting techniques.

The foregoing method results in a qualitative as well as quantitative assay for total prostaglandins of the E and F series.

The biological sample which would typically be assayed by the present method includes all conventional biological samples such as, for example, blood, urine, tissue, etc.

In order to guard against loss of prostaglandins in a sample, e.g. by degradation, an internal standard can be used. For example, a known amount of $^{14}C$ labeled $PGE_2$ or $^{14}C$ $PGF_{2\alpha}$ may be added to the sample prior to the assay and counted at the end of the procedure. The percent reduction of $^{14}C$ $PGE_2$ or $^{14}C$ $PGF_{2\alpha}$ from the known amount placed in the sample indicates the percent of $PGE_2$ or $PGF_{2\alpha}$ lost during the assay procedure. Other similar internal standards may be used.

In order to minimize interference of background radiation caused by exchange of $^3H$ atoms for $^1H$ atoms in water present in the assay sample, the water remaining in the reaction sample is preferably removed by any convenient method, e.g. a deliquescent substance such as magnesium sulfate can be added to the sample.

In order to aid in visualization of the labeled prostaglandins in the separation step 4, known unlabeled prostaglandins may be added just prior to step 4.

The following Examples are for the purpose of illustration and it is understood that the invention is not to be limited to the reagents or conditions set forth.

EXAMPLE I

A biological sample such as 1.0 ml of urine to which 0.25 ngrams of $PGE_2$ and 0.25 ngrams $PGF_{2\alpha}$ as well as 2500 CPM of pure $^{14}C$-$PGE_2$ (which serves as an internal standard) has been added is extracted twice with an equal volume of ethyl acetate. The combined extracts are taken to dryness under vacuum. The residue is subsequently dissolved in 10 ml of methanol to which 100 mg of $NaBH_4$ is added. After reaction for 30 minutes at 25°C, the excess $NaBH_4$ is destroyed with a stoichiometric amount of $H_2SO_4$. The reaction mixture is again extracted with ethyl acetate, the extract again taken to dryness and subsequently dissolved in a minimal amount of ethanol.

To the ethanol solution, 2.0 ml of a solution containing 10 mg of crude 15-hydroxy prostaglandin dehydrogenase, 25 mM $NAD^+$, 50 mM Tris.HCl, 50 mM KCl, 10 mM $MgCl_2$, and 7 mM mercaptoethanol, all at pH - 8.6, is added. The reaction is allowed to proceed at 37°C for 1 hour. The crude enzyme is prepared by making a 25% homogenate of swine lung (using a Waring blender) in 0.1M sodium phosphate buffer containing 7 mM mercaptoethanol. All enzyme preparation steps are carried out at 4°C. Via differential centrifugation, a 105,000 Xg is prepared. This supernatant is subsequently fractionated with ammonium sulfate, with the 20–45% wt containing the desired activity. The precipitate is resuspended in 50 mM Tris.HCl buffer (pH = 8.6) and dialyzed prior to use.

The enzymatic reaction is terminated by acidification (0.2 ml of 1.0N HCl) and then extracted twice with equal volumes of ethyl acetate. The extracts are combined, the ethyl acetate removed by vacuum and the residue is dissolved in ethanol. Sodium borotritide ($10^{-9}$ gram) (20 Ci/mmole) is added and the reaction is allowed to proceed for 30 minutes at 25°C. The reaction mixture is spotted along with a standard mixture of cold $PGE_2$ and $PGF_{2\alpha}$ (5 μg each) on silica gel TLC plates and developed in a solvent system consisting of the organic phase of ethyl acetate-iso-octane-glacial acetic acid-water (110:50:20:100). The TLC plates are visualized with iodine vapor and the reaction product scraped. The radioactivity is measured by a standard scintillation counter. Appropriate calculations are made to determine the reaction efficiency of the original $PGE_2$ added as well as to determine the total PGE and PGF content of the original sample. An overall recovery of approximately 50% is obtained. Maximum sensitivity of the system is 0.1–0.25 ngram of prostaglandin E/F.

I claim:

1. A method for assaying prostaglandins of the E and F series comprising the sequential steps of reducing the keto groups in a sample containing the prostaglandins to hydroxy groups, selectively oxidizing the prostaglandin 15-OH groups to keto groups, reducing the keto groups to hydroxy groups by means of a radioactive labeled chemical reducing agent, isolating radioactive labeled prostaglandins and measuring the amount of radioactivity of the isolated radioactive labeled prostaglandins.

2. The method of claim 1 wherein first reduction is carried out by reacting the sample with sodium borohydride.

3. The method of claim 1 wherein the selective oxidation of the prostaglandin 15-OH groups is carried out by reacting the sample with 15-hydroxy prostaglandin dehydrogenase.

4. The method of claim 1 wherein the second reduction is carried out by reacting the sample with sodium borotritide.

5. The method of claim 1 wherein the radioactive labeled prostaglandins are separated by thin layer chromatography.

6. A method for assaying prostaglandins of the E and F series comprising the sequential steps of reacting a sample containing prostaglandins with sodium borohydride under conditions sufficient to reduce all keto groups in the sample to hydroxy groups, reacting the sample with 15-hydroxy prostaglandin dehydrogenase under conditions sufficient to oxidize all prostaglandin 15-OH groups to prostaglandin 15-oxy groups, reacting the sample with sodium borotritide under conditions sufficient to reduce all keto groups in the sample to hydroxy groups, isolating the tritiated prostaglandins and measuring the amount of radioactivity of the isolated tritiated prostaglandins.

7. The method of claim 6 wherein the tritiated prostaglandins are isolated by thin layer chromatography.

8. The method of claim 6 having the additional step of removing any water present in the reaction mixture before isolating the tritiated prostaglandins.

9. The method of claim 6 wherein an internal standard is used.

10. The method of claim 9 wherein the internal standard is $^{14}C$ labeled prostaglandin E or $^{14}C$ labeled prostaglandin F.

* * * * *